United States Patent
Ali et al.

(10) Patent No.: US 11,319,331 B2
(45) Date of Patent: May 3, 2022

(54) PROBE FOR SELECTIVE DETECTION OF HYPOCHLOROUS ACID (HOCL) UNDER PHYSIOLOGICAL CONDITION, AND RELATED METHODS

(71) Applicant: Council of Scientific & Industrial Research, Delhi (IN)

(72) Inventors: Firoj Ali, Pune (IN); Sunil Babanrao Aute, Pune (IN); Anila Hoskere Ashok, Pune (IN); Suman Pal, Pune (IN); Amitava Das, Bhavnagar (IN)

(73) Assignee: Council of Scientific & Industrial Research, New Delhi (IN)

( * ) Notice: Subject to any disclaimer, the term of this patent is extended or adjusted under 35 U.S.C. 154(b) by 358 days.

(21) Appl. No.: 16/609,423

(22) PCT Filed: May 8, 2018

(86) PCT No.: PCT/IN2018/050281
§ 371 (c)(1),
(2) Date: Oct. 29, 2019

(87) PCT Pub. No.: WO2018/207203
PCT Pub. Date: Nov. 15, 2018

(65) Prior Publication Data
US 2020/0102330 A1   Apr. 2, 2020

(30) Foreign Application Priority Data

May 8, 2017   (IN) .............................. 201711016120

(51) Int. Cl.
*G01N 21/00*   (2006.01)
*C07F 5/02*   (2006.01)
*G01N 21/76*   (2006.01)

(52) U.S. Cl.
CPC ............. *C07F 5/022* (2013.01); *G01N 21/76* (2013.01)

(58) Field of Classification Search
CPC ...................................................... C07F 5/022
USPC ....................................................... 436/101
See application file for complete search history.

(56) References Cited

PUBLICATIONS

Chen et al., "A highly selective turn-on fluorescent probe for hypochlorous acid based on hypochlorous acid-induced oxidative intramolecular cyclization of boron dipyrromethene-hydrazone," Analytica. Chimica. Acta., vol. 882, (2015), pp. 68-75.
Firoj Ali et al: "A fluorescent probe for specific detection of cysteine in the lipid dense region of cells", Chemical Communications, vol. 51, No. 95, Jan. 1, 2015 (Jan. 1, 2015), pp. 16932-16935.
Firoj Ali et al: "Tracking HOCl concentrations across cellular organelles in real time using a super resolution microscopy probe", Chemical Communications, vol. 54, No. 15, Jan. 1, 2018 (Jan. 1, 2018), pp. 1849-1852.
Hong-Wen Liu et al: "A red emitting two-photon fluorescent probe for dynamic imaging of redox balance meditated by a superoxide anion and GSH in living cells and tissues", The Analyst, vol. 141, No. 20, Jan. 1, 2016 (Jan. 1, 2016), pp. 5893-5899.
International Search Report for International Application No. PCT/IN2018/050281, dated Aug. 9, 2018, 3 pages.

(Continued)

*Primary Examiner* — Christine T Mui
*Assistant Examiner* — Emily R. Berkeley
(74) *Attorney, Agent, or Firm* — TraskBritt (57) ABSTRACT

The present disclosure shows a molecular probe SF-1 which is useful for selective detection of hypochlorous acid (HOCl) over other reactive oxygen species (ROS) and a process for the preparation thereof.

10 Claims, 8 Drawing Sheets

(56) References Cited

PUBLICATIONS

International Written Opinion for International Application No. PCT/IN2018/050281, dated Aug. 9, 2018, 9 pages.

Jiyoung Kim et al: "A water-soluble sulfonate-BODIPY based fluorescent probe for selective detection of HOCl/OCl-in aqueous media", The Analyst, vol. 139, No. 12, Jan. 1, 2014 (Jan. 1, 2014), pp. 2986-2989.

Jun Jacob Hu et al: "HKOCl-2 Series of Green BODIPY-Based Fluorescent Probes for Hypochlorous Acid Detection and Imaging in Live Cells", Organic Letters, vol. 16, No. 13, Jun. 20, 2014 (Jun. 20, 2014), pp. 3544-3547.

Liang et al., "Highly Selective and Sensitive Photoinduced Electron Transfer (PET) Based HOCl Fluorescent Probe in Water and Its Endogenous Imaging in Living Cells," Chemical Communications, vol. 52, (2016), pp. 7982-7985.

Mulay et al., "Enhanced Fluorescence Turn-on Imaging of Hypochlorous Acid in Living Immune and Cancer Cells," Chemistry—A European Journal, vol. 22, (2016), pp. 9642-9648.

Sun et al., "A Highly Specific BODIPY-Based Fluorescent Probe for the Detection of Hypochlorous Acid," Organic Letters, vol. 10, (2008), pp. 2171-2174.

Sunil Aute et al: "Demonstrating the role of anchoring functionality in interfacial electron transfer dynamics in the newly synthesized BODIPY-TiO 2 nanostructure composite", New Journal of Chemistry, vol. 41, No. 12, Jan. 1, 2017 (Jan. 1, 2017), pp. 5215-5224.

Zhu et al., "An "Enhanced PET"-Based Fluorescent Probe with Ultrasensitivity for Imaging Basal and Elesclomol-Induced HClO in Cancer Cells," American Chemical Society, vol. 136, (2014), pp. 12820-12823.

PROBE FOR SELECTIVE DETECTION OF HYPOCHLOROUS ACID (HOCL) UNDER PHYSIOLOGICAL CONDITION, AND RELATED METHODS

CROSS-REFERENCE TO RELATED APPLICATIONS

This application is a national phase entry under 35 U.S.C. § 371 of International Patent Application PCT/IN2018/050281, filed May 8, 2018, designating the United States of America and published in English as International Patent Publication WO 2018/207203 A1 on Nov. 15, 2018, which claims the benefit under Article 8 of the Patent Cooperation Treaty to Indian Patent Application Serial No. 201711016120, filed May 8, 2017.

TECHNICAL FIELD

The present disclosure relates to a molecular probe for detection of hypochlorous acid. Particularly, the present disclosure relates to a molecular probe SF-1, useful for selective detection of hypochlorous acid (HOCl) over other reactive oxygen species (ROS) under physiological condition and a process for the preparation thereof.

BACKGROUND

Bio-imaging technologies to probe the molecular basis of life are in demand. In this context, optical microscopy has proven utility and versatility. Luminescent probes for specific biomolecules and cellular structures are particularly attractive as they provide increased contrast over traditional techniques. The ideal characteristics of cell-permeable probes are that they display low toxicity, organelle specificity, and are photostable with a bright emission.

Optical microscopy has been used to investigate cellular processes and cellular response to reactive oxygen species (ROS). ROS are involved in a range of m cell signaling and regulation processes and dysfunctions that leads to degenerative diseases and cancers. A panoply of processes involved in homeostasis and cell activation is controlled by regulation of the concentration and location of specific ROS. HOCl is an important ROS, which is naturally produced by the myeloperoxidase-$H_2O_2$-Cl_ system. This species is catabolized through oxidation by glutathione and cellular thiols and plays a key role in cell death signaling. Thus, detection of HOCl signaling, will plays a key role in understanding the intricacies of these complicated biological mechanisms. HOCl also plays an important role in the immune response to pathogens, as it is generated during phagocytosis. Activated phagocytic cells generate HOCl as part of the inflammation response. Its overproduction is associated with cardiovascular disease, a neurodegenerative disorder, and inflammatory-related diseases. These effects may be due to quite specific cellular mechanisms; for example, it is suggested that HOCl plays a part in the Golgi stress response, a phenomenon linked to a number of neurodegenerative diseases. However, the role of the Golgi apparatus in HOCl induced oxidative stress is still unclear due to lack of suitable probes. To fully understand such signaling processes, dedicated HOCl probes that display localization in specific cellular compartments are urgently required.

Article titled "A water-soluble sulfonate-BODIPY based fluorescent probe for selective detection of HOCl/OCl⁻ in aqueous media" by J Kim et al. published in Analyst, 2014, 139, 2986-2989 reports a new, water-soluble BODIPY dye 1, bearing sulfonate groups at the 2- and 6-positions was found to be a sensitive and selective fluorescent probe for the detection of HOCl/OCl⁻ in aqueous buffer solution. The probe, which displays extremely weak fluorescence owing to efficient singlet excited state quenching by photoinduced electron transfer (PeT) from an electron-rich catechol group at a meso-position, responds to HOCl/OCl⁻ through a dramatic enhancement of its fluorescence intensity. This finding indicates that the probe can be utilized to detect HOCl/OCl quantitatively. The detection limit was reported to be 0.3 mM (S/N ¼ 3).

Article titled "A fluorescent probe for specific detection of cysteine in the lipid dense region of cells" by Firoj Ali et al. published in Chem. Commun., 2015, 51, 16932-16935 reports a new cysteine (Cys) specific chemodosimetric reagent (ER-F) is used in imaging of endogenous Cys localized in the lipid dense region of the live Ht116 cells and the release of Cys within HepG2 cells from a drug following a biochemical transformation.

Article titled "A Highly Specific BODIPY-Based Fluorescent Probe for the Detection of Hypochlorous Acid" by ZN Sun et al. published in Org. Lett., 2008, 10 (11), pp 2171-2174 reports a fluorescent probe, HKOCl-1, has been successfully developed for the detection of hypochlorous acid on the basis of a specific reaction with p-methoxyphenol. The formation of HOCl has been successfully detected not only in an abiotic system but also in an enzymatic system (myeloperoxidase/$H_2O_2$/Cl⁻ system) and in living macrophage cells upon stimulation. This new probe might be used as an efficient tool for probing the roles HOCl plays in biological systems.

Article titled "A highly selective and sensitive photoinduced electron transfer (PET) based HOCl fluorescent probe in water and its endogenous imaging in living cells" by L Liang et al. published in Chem. Commun., 2016, 52, 7982-7985 reports a probe based on the phenothiazine-acridine orange conjugate (Ptz-AO) has been designed and synthesized for the sensitive and selective detection of HOCl. Ptz-AO has excellent properties, including pH-independence of fluorescence, high resistance to photobleaching, and response in real time. The probe shows high selectivity, high sensitivity (detection limit of 2.7 nM) and fast response (within 5 seconds) towards HOCl in water. The marvelous sensing properties of the probe Ptz-AO enable its use in the living cells for the real-time monitoring of HOCl in INS-1 b-islet cells and RAW 264.7 macrophage cells.

Article titled "HKOCl-2 Series of Green BODIPY-Based Fluorescent Probes for Hypochlorous Acid Detection and Imaging in Live Cells" by J J Hu et al. published in Org. Lett., 2014, 16 (13), pp 3544-3547 reports a HKOCl-2 series of new fluorescent probes for hypochlorous acid (HOCl) detection in live cells. The probes exhibit excellent selectivity, sensitivity, and chemostability toward HOCl. In particular, HKOCl-2b rapidly and selectively detects endogenous HOCl in both human and mouse macrophages. These probes could therefore serve as promising discovery tools to help elucidate biological functions of HOCl. The detection limit (S/N=3) was estimated to be 42, 18, and 37 nM for HKOCl-2a, HKOCl-2b, and HKOCl 2c, respectively.

Article titled "An "Enhanced PET"-based fluorescent probe with ultrasensitivity for imaging basal and elesclomol-induced HClO in cancer cells" by H Zhu et al. published in J. Am. Chem. Soc., 2014, 136 (37), pp 12820-12823 reports a BODIPY-based HClO probe (BClO) with ultrasensitivity, fast response (within 1 s), and high selectivity, in which the pyrrole group at the meso position has an "enhanced PET" effect on the BODIPY fluorophore. The detection limit is as low as 0.56 nM, which is the highest sensitivity achieved to date. BClO can be facilely synthesized by a Michael addition reaction of acryloyl chloride with 2,4-dimethylpyrrole and applied to image the basal HClO in cancer cells for the first time and the time-dependent HClO generation in MCF-7 cells stimulated by elesclomol, an effective experimental ROS-generating anticancer agent. However, this work is more focused on imaging of basal HOCl and monitoring the time dependent elevation of HOCl caused by elesclomol in MCF-7 Cells. This probe is not organelle specific.

Article titled "A highly selective turn-on fluorescent probe for hypochlorous acid based on hypochlorous acid-induced oxidative intramolecular cyclization of boron dipyrromethene-hydrazone" by WC Chen et al. published in *Analytica Chimica Acta;* 2015, 882, pp 68-75 reports a BODIPY-based fluorescent probe, HBP, developed for the detection of hypochlorous acid based on the specific hypochlorous acid-promoted oxidative intramolecular cyclization of heterocyclic hydrazone in response to the amount of HOCl. The reaction is accompanied by a 41-fold increase in the fluorescent quantum yield (from 0.004 to 0.164). The fluorescence intensity of the reaction between HOCl and HBP is linear in the HOCl concentration range of 1-8 µM with a detection limit of 2.4 nM (S/N=3). Confocal fluorescence microscopy imaging using RAW264.7 cells showed that the new probe HBP could be used as an effective fluorescent probe for detecting HOCl in living cells.

Article titled "Enhanced fluorescence turn-on imaging of hypochlorous acid in living immune and cancer Cells" by S V Mulay et al. published in *Chemistry;* 2016; 22(28); pp 9642-9648 reports two closely related phenyl selenyl based boron-dipyrromethene (BODIPY) turn-on fluorescent probes for the detection of hypochlorous acid (HOCl) synthesized for studies in chemical biology; emission intensity is modulated by a photoinduced electron-transfer (PET) process. The fluorescence intensity of probes 1 and 2 with HOCl involves an ~18 and ~50-fold enhancement compared with the respective responses from other reactive oxygen/nitrogen species (ROS/RNS) and low detection limits (30.9 nm for 1 and 4.5 nm for 2). Both probes show a very fast response with HOCl; emission intensity reached a maximum within 1 s. These probes show high selectivity for HOCl, as confirmed by confocal microscopy imaging when testing with RAW264.7 and MCF-7 cells. The reported probe can detect HOCL in presence of EtOH-phosphate buffer saline (PBS) medium at pH 7.4.

Until now, biological activity of HOCl is hardly known due lack of appropriate imaging reagents which can detect endogenous HOCl selectively inside living cells. Further, the reported probes suffer from the drawbacks like low detection limit, detection is done in medium which are not advisable for the detection of HOCl in biological objects and bio sample (like blood plasma) studies. Therefore, there is a need to develop a new effective probe which is capable of detecting hypochlorous acid (HOCl) over other reactive oxygen species (ROS).

BRIEF SUMMARY

The present disclosure provides a molecular probe SF-1.

In another embodiment, the disclosure provides a molecular probe SF-1, useful for selective detection of hypochlorous acid (HOCl) over other reactive oxygen species (ROS) under physiological condition.

In another embodiment, the disclosure provides a process for the preparation of the probe SF-1.

Accordingly, the present disclosure provides a compound of formula SF-1

In an embodiment of the present disclosure, the compound is used for selective detection of hypochlorous acid (HOCl) over other reactive oxygen species (ROS) under physiological condition.

In another embodiment of the present disclosure, the compound of formula SF-1 is used for HOCl detection in live RAW 264.7 macrophages.

In yet another embodiment of the present disclosure, the detection limit for HOCl is in the range of 4 to 5 nM in aq. PBS buffer-acetonitrile.

In yet another embodiment, the present disclosure provides a process for the preparation of compound of formula SF-1 comprising the act of:
 i. refluxing BODIPY derivative, 3,4-Dihydroxy benzaldehyde, glacial acetic acid and piperidine in a solvent at a temperature ranging from 110° to 120° C. for the period ranging from 3 to 4 hours to afford compound of formula SF-1.

In still another embodiment of the present disclosure, the BODIPY derivative used is 5,5-difluoro-1,3,7,9-tetramethyl-10-phenyl-5H-4λ$^4$,5λ$^4$-dipyrrolo[1,2-c:2',1'-f][1,3,2]diazaborinine.

In still another embodiment of the present disclosure, solvent used is toluene.

In still another embodiment, the present disclosure provides a kit for the detection of HOCl comprising at least compound of formula SF-1.

In still another embodiment, the present disclosure provides a method of detection of HOCl in biological systems using compound of formula SF-1.

DETAILED DESCRIPTION

The present disclosure provides a molecular probe SF-1, which is useful for selective detection of hypochlorous acid (HOCl) over other reactive oxygen species (ROS) under physiological condition and process for preparation thereof.

SF-1

The probe SF-1 is capable of detecting hypochlorous acid (HOCl) selectively over other reactive oxygen species (ROS) under physiological condition with an instant turn on fluorescence response. The probe SF-1 specifically detects HOCl at neutral pH and at physiological condition. The response of said probe SF-1 towards HOCl is very fast so it can be used in rapid probing of HOCl, insitu generated by an enzymatic assay as well as chemical reactions. The molecular probe SF-1 exclusively shows fluorescence ON response to HOCl and endogenously generated HOCl in RAW 264.7 macrophages.

The present disclosure provides a process for the preparation of said probe SF-1 comprising refluxing BODIPY derivative, 3,4-Dihydroxy benzaldehyde, glacial acetic acid, piperidine in suitable solvent at the temperature ranging from 110° to 120° C. for the time period ranging from 3 to 4 hours to afford probe SF-1.

The BODIPY derivative is 5,5-difluoro-1,3,7,9-tetramethyl-10-phenyl-5H-4$\lambda^4$,5$\lambda^4$-dipyrrolo[1,2-c:2',1'-f][1,3,2]diazaborinine. The solvent of step (b) is selected from toluene.

The compound of formula (SF-1) is used for HOCl detection in live RAW 264.7 macrophages.

The detection limit for HOCl is in the range of 4 to 5 nM in aq. PBS buffer-acetonitrile.

The present disclosure provides a process for the preparation of probe SF-1 comprises refluxing BODIPY derivative, 3,4-Dihydroxy benzaldehyde, glacial acetic acid, piperidine in suitable solvent at the temperature ranging from 110° to 120° C. for the time period ranging from 3 to 4 hours to afford probe SF-1.

Figure 13:
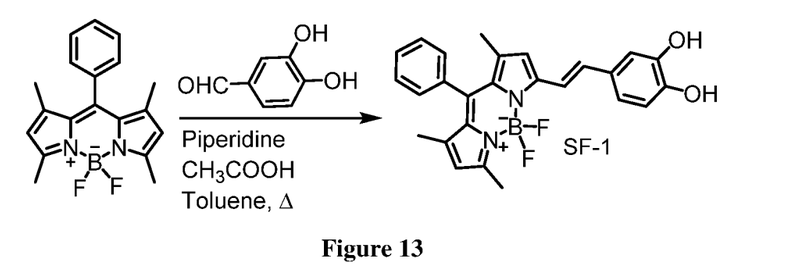
FIG. 13 represents the process for the preparation of probe SF-1.

The process for the preparation of said probe SF-1 is shown in Scheme 1.

Figure 14:
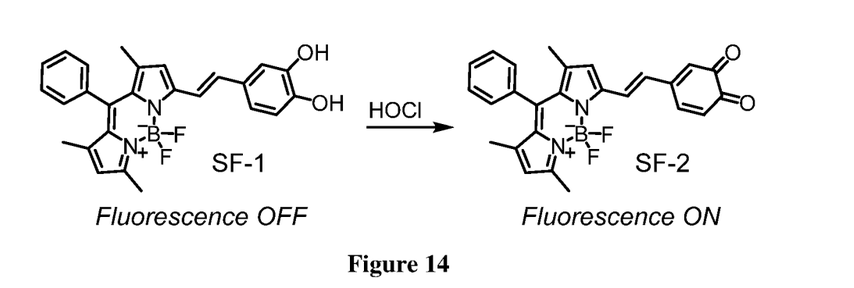
FIG. 14 represents the proposed sensing mechanism of SF-1 with HOCl.

In one embodiment, the present disclosure provides a method of detection of hypochlorous acid (HOCl) in biological systems using compound of formula (SF-1). The proposed sensing mechanism of SF-1 with HOCl is depicted in scheme 2.

Figure 1:
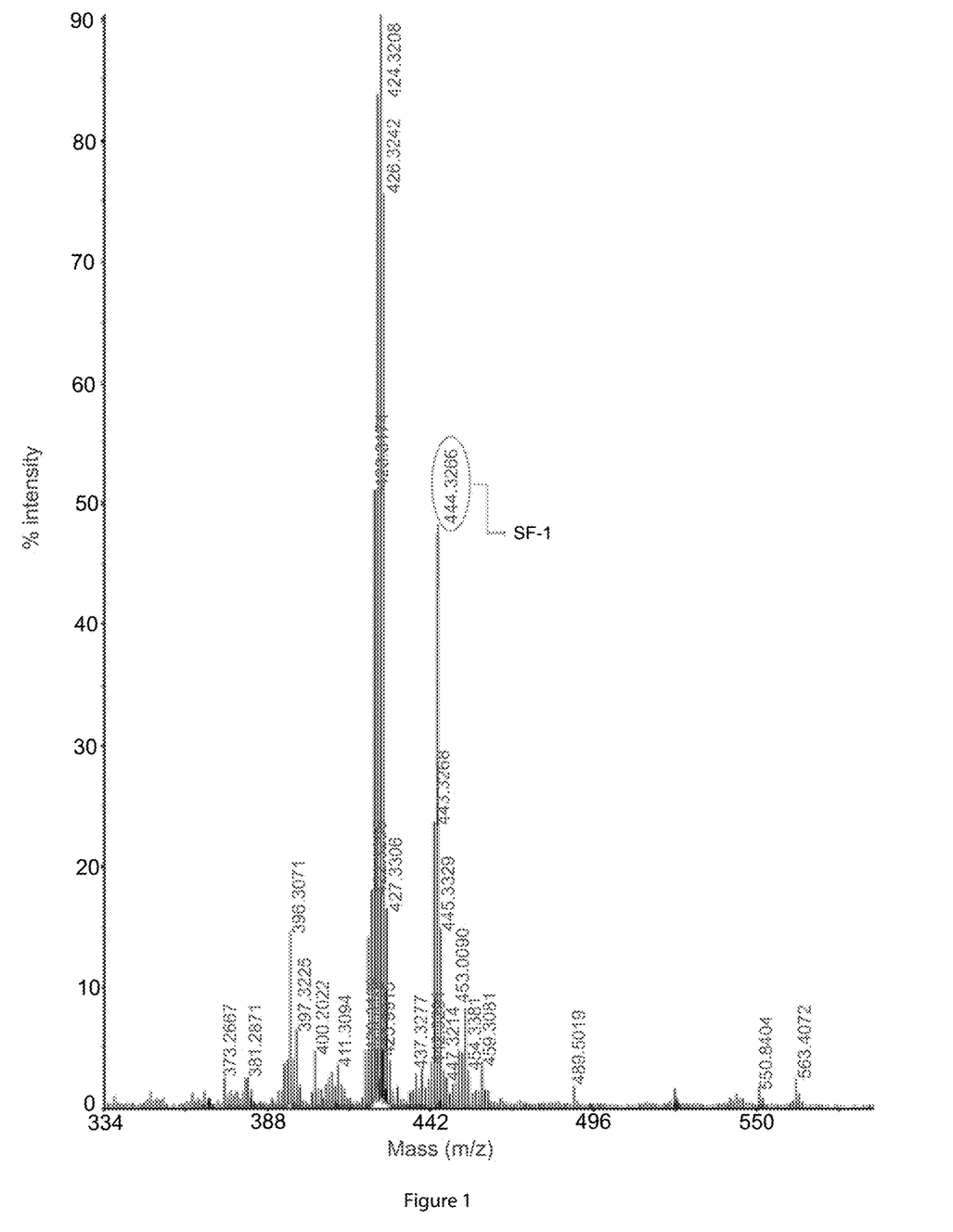
FIG. 1: MALDI-MS spectrum of SF-1.
Figure 2:
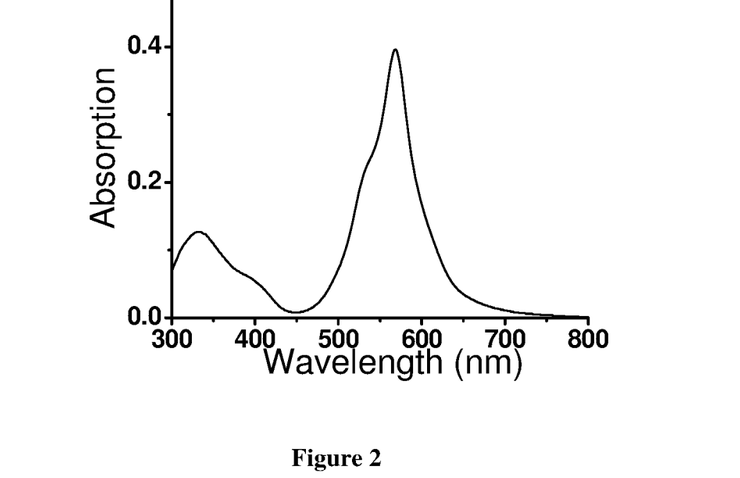
FIG. 2: UV-Vis spectra of SF-1.
Figure 3:
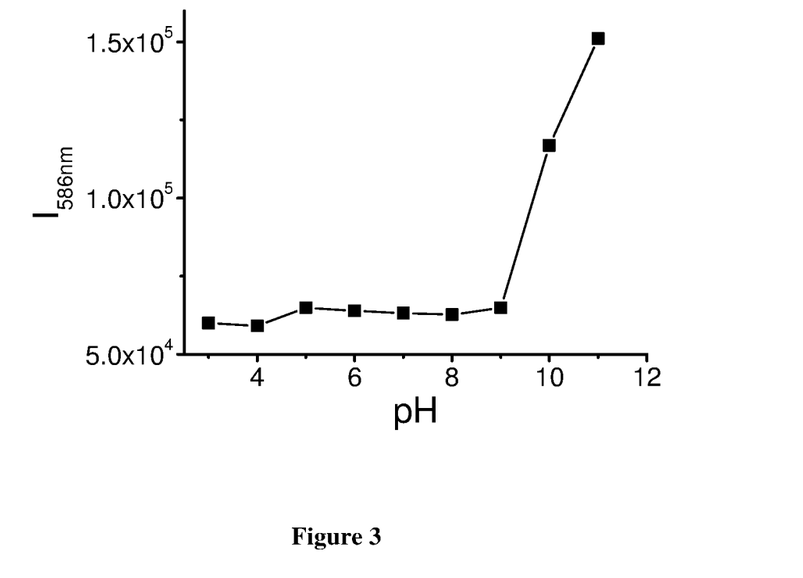
FIG. 3: pH response of SF-1.
Figure 4:
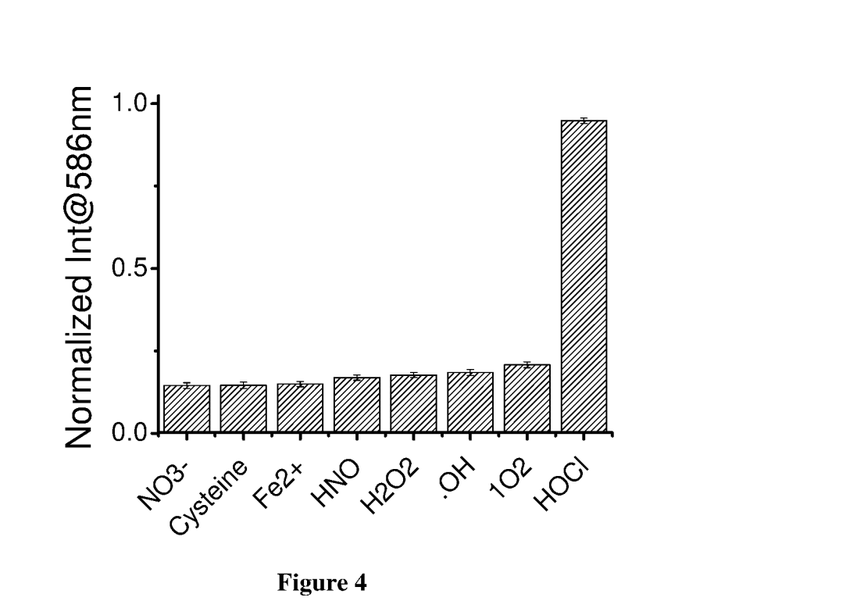
FIG. 4: Selectivity studies of SF-1, Emission response of SF-1 (10 µM) in the absence and presence of various Reactive analytes in Acetonitrile: PBS with pH 7.2.

FIG. 4 depicts emission response of SF-1 (10 μM) in the absence and presence of various Reactive analytes (200 mole equiv. each) in Acetonitrile: PBS (1:9, v/v) with pH 7.2.

Figure 5:
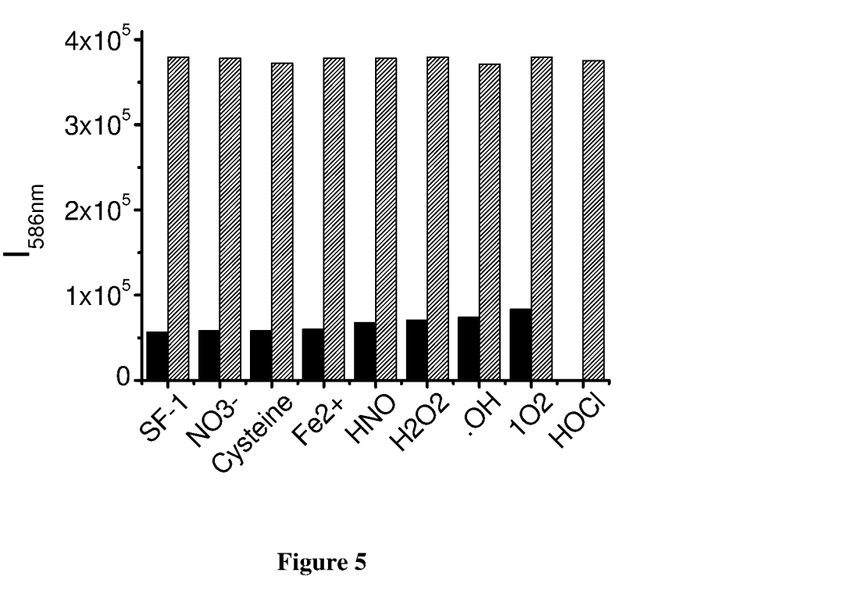
FIG. 5: Changes in emission intensity of SF-1 induced by HOCl in the presence of other analytes.

FIG. 5 depicts changes in emission intensity of SF-1 (10 μM) induced by HOCl (2 mM) in the presence of (2 mM) of other analytes. Cross line bar and black bar represent emission response in the presence and absence of HOCl, respectively. $\lambda_{Ext}$=550 nm, $\lambda_{Mon}$=586 nm.

Figure 6:
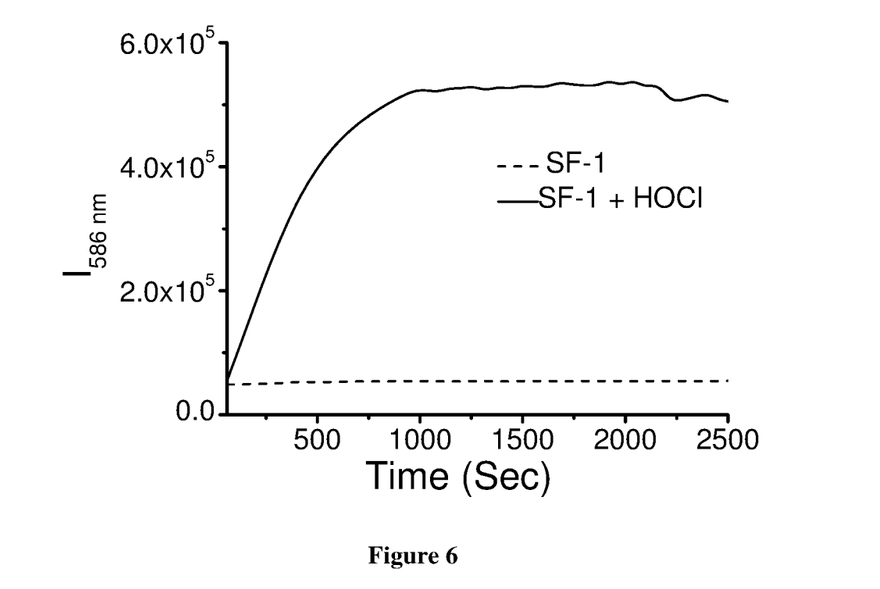
FIG. 6: Time dependent response of HOCl with SF-1.

FIG. 6 depicts Time dependent emission studies of SF-1 (10 μM) in absence and presence of 2 mM HOCl in PBS—Acetonitrile medium (9:1, v/v) of pH 7.2 at 37° C. $\lambda_{Ext}$=550 nm. $\lambda_{Mon}$=586 nm. Accordingly, all studies are carried out at physiological relevant pH 7.4. Time dependent luminescence assay of the probe SF-1 (10 μM) is carried out in presence of 2 mM HOCl (FIG. 6), which reveals that the reaction of SF-1 with HOCl complete within 15 min and formed luminescence ON BODIPY derivative SF-2 having expanded quinone moiety. ESI-MS spectra and $^{13}$C NMR spectra of SF-1, in the presence of HOCl supported the formation of SF-2 and this facilitates the sensing mechanism shown in scheme 2, which are better results than with the previous results.

Figure 7:
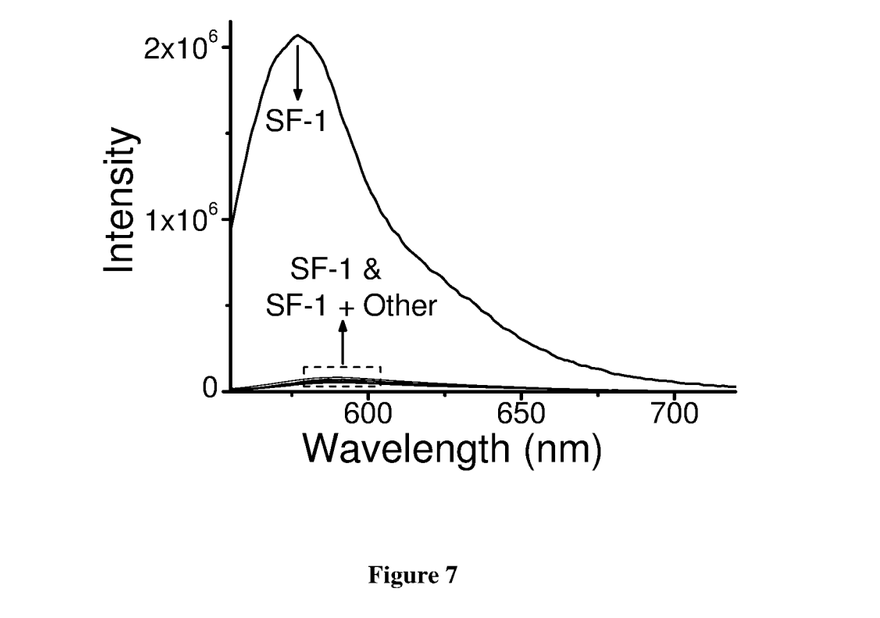
FIG. 7: Change in emission spectra of SF-1 in presence and absence of different ROS.
Figure 8:
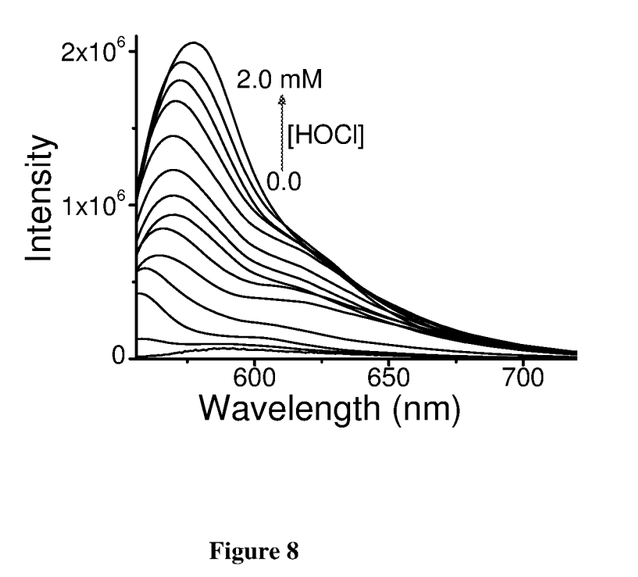
FIG. 8: Emission titration profile plot of SF-1 with various concentration of HOCl.

FIG. 7 depicts the detailed luminescence response of probe SF-1 is investigated with HOCl.

To examine the in vitro selectivity of probe SF-1 towards different reactive oxygen species (ROS) and reactive nitrogen species (RNS), luminescence spectral response of SF-1 are recorded in presence of 20 mole equivalent of various ROS/RNS and some other bio-analytes as well in PBS-acetonitrile (9:1, v/v) medium. No observable luminescence signal is observed in presence of various ROS/RNS except HOCl. A turn ON luminescence response of SF-1 is observed for HOCl with an emission maximum at 585 nm, upon $\lambda_{Ext}$ at 550 nm, shown in FIG. 7 shows an enhancement of luminescence intensity at $\lambda_{Em}^{Max}$ 580 nm [quantum yield (QY)=0.0257, $\lambda_{Ext}$=540 nm] by 20 fold with increasing dose of HOCl is observed. Luminescence intensity of SF-1 is linearly propersonal with lower concentration range 0-20 μM and lower detection limit is found to be 4.3 nM in aqueous buffer medium. Moreover, luminescence spectra of SF-1 are also recorded at different pH, which revealed that SF-1 is quite stable in aqueous solution with the pH range 4-9.

Figure 9:
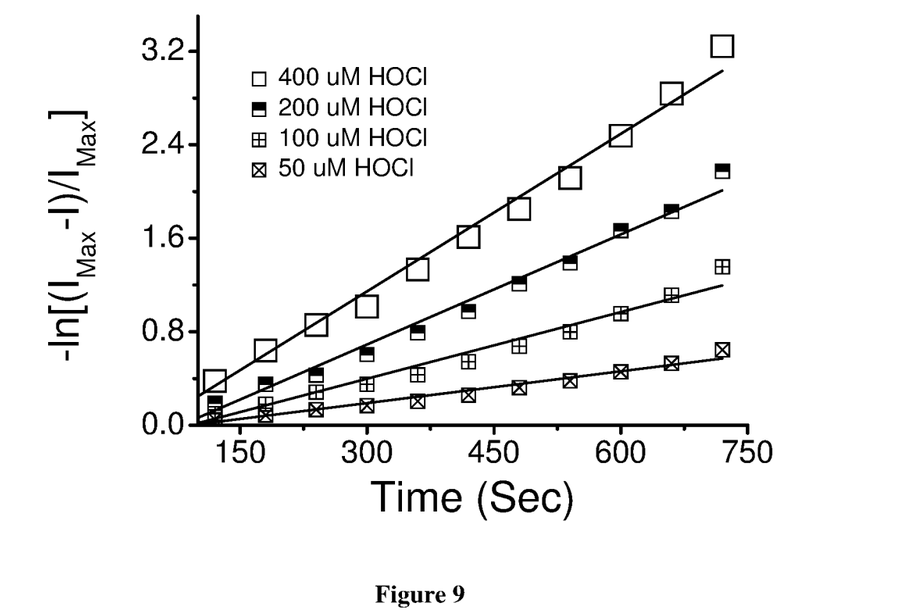
FIG. 9: Plots of the $\ln[I_{Max}-I_0]/I_{Max}$ as a function of time for evaluation of respective kobs for certain [HOCl].

FIG. 9 depicts plots of the $\ln[I_{Max}-I_0]/I_{Max}$ as a function of time for evaluation of respective kobs for certain [HOCl].

Figure 10:
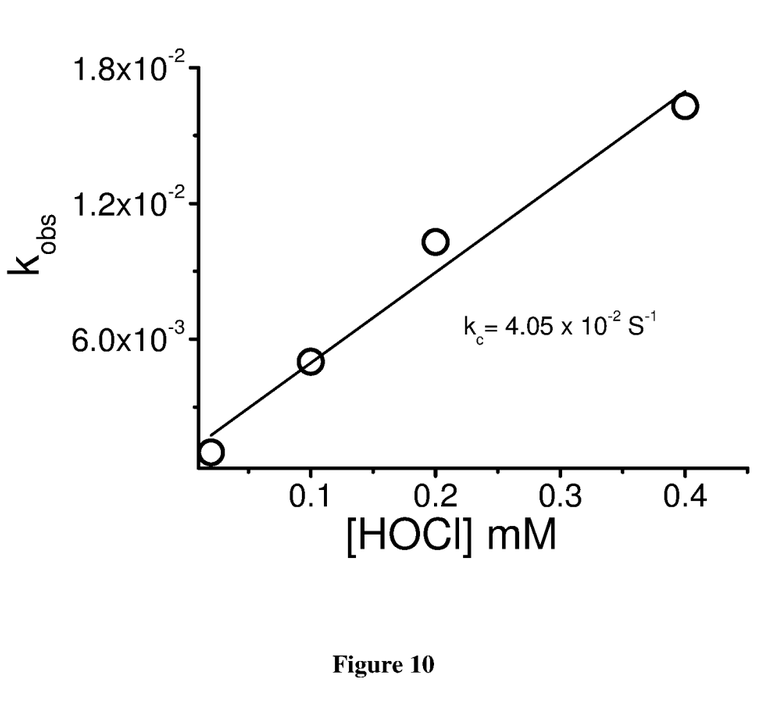
FIG. 10: Plot for the kobs with varying [HOCl] for the evaluation of rate constant (k) for the reaction between SF-1 and HOCl.

FIG. 10 depicts plot for the Kobs with varying [HOCl] for the evaluation of rate constant (k) for the reaction between SF-1 and HOCl.

It is observed that, even with large excesses of other ROS/RNS and intracellular enzymes like tryosinase, the emission response of SF-1 remains unchanged, illustrating its specificity towards HOCl. The lowest detection limit is evaluated using 3 s method to be 4.3 nM in aq. PBS buffer-acetonitrile (9:1, v/v) solution. Further studies confirmed that SF-1 is stable across a wide pH range (pH=4-9). Time-dependent luminescence assays employing 10 mM solutions of the probe in the presence of 2 mM HOCl, reveal that the reaction is completed within 15 min. The HRMS data clearly indicate that reagent SF-1 reacts with HOCl to produce SF-2. The higher emission quantum yield for SF-2 is attributed to an interrupted CT process and enhanced HOMO-LUMO energy gap.

Figure 11:
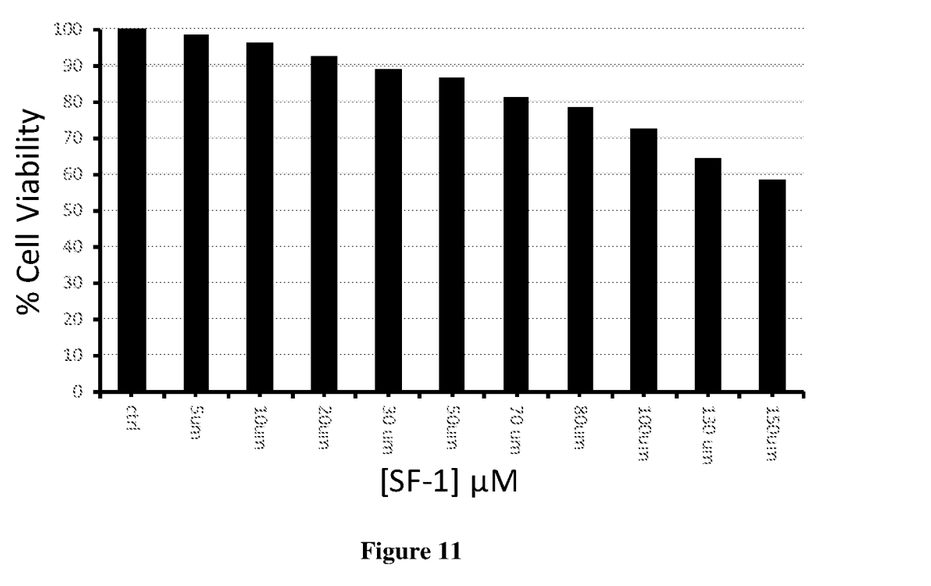
FIG. 11: MTT assay to determine the cell viability percentage in presence of SF-1 in RAW 264.7 cells. IC50 was found to be >150 μM.
Figure 12:
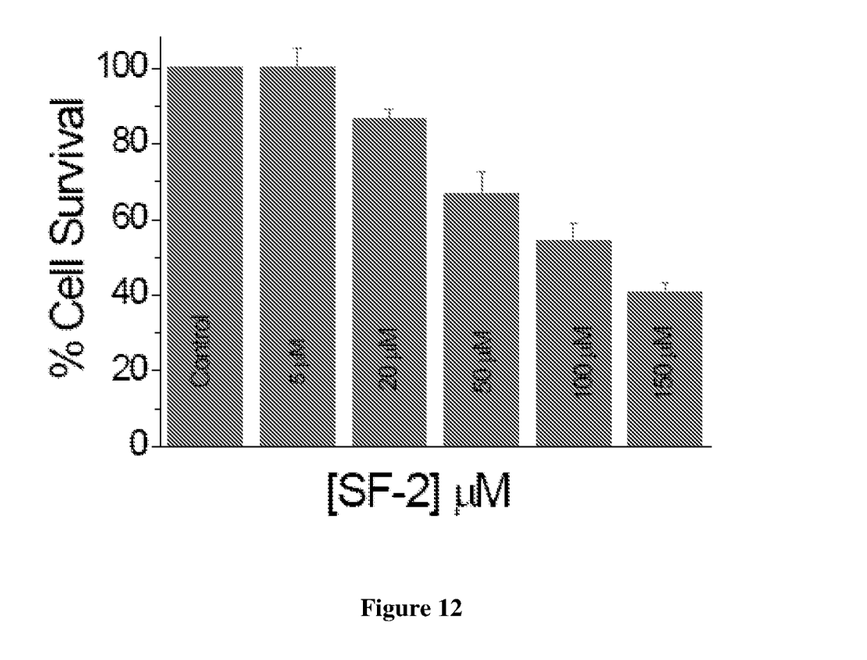
FIG. 12: MTT assay to determine the cell viability percentage in presence of SF-2 in RAW 264.7 cells. IC50 was found to be 110 μM.

The MTT assays confirmed that both SF-1 and SF-2 are non-toxic towards RAW 264.7 macrophage cells (FIGS. 11 and 12).

The present disclosure provides a kit for the detection of hypochlorous acid (HOCl) comprising at least compound of formula (SF-1).

The present disclosure provides a method of detection of HOCl in biological systems using compound of formula (SF-1).

EXAMPLES

Following examples are given by way of illustration therefore should not be construed to limit the scope of the disclosure.

General

All commercial reagents were procured from suppliers, were used as received without further purification. Solvents were dried as and when required by using standard procedures. OH radical was generated by Fenton reaction of $FeSO_4$ and $H_2O_2$ and singlet $^1O_2$ was generated by the reaction of $H_2O_2$ and NaOCl. $^1H$ and $^{13}C$ NMR spectra were recorded on Bruker 400/500 MHz FT NMR (Model: Advance-DPX 400/500) using TMS as an internal standard. All the Fluorescence measurements were carried out on a spectrofluorometer and, in particular, a PTI QUANTAMASTER™ Steady State Spectrofluorometer. ESI-Mass spectra were recorded on JEOL JM AX 505 HA mass spectrometer. UV-Vis spectra were recorded using Shimadzu UV-1800 spectrometer. Quantum yield was recorded using standard methods and rhodamine B as standard. All the Structured Illumination Microscopy (SIM) and Wide Field Fluorescence Microscopy experiments were performed by using an illumination microscope and, in particular, a DELTAVISION™ OMX-SIM (GE Health care). The Post processing SIM reconstructions were performed by using Soft Worx software.

Example 1: Synthesis of E)-4-(2-(5,5-difluoro-1,7,9-trimethyl-10-phenyl-5H-5λ$^4$,6λ$^4$-dipyrrolo[1,2-c:2',1'-f][1,3,2]diazaborinin-3-yl)vinyl)benzene-1,2-diol (SF-1)

A mixture of 5,5-difluoro-1,3,7,9-tetramethyl-10-phenyl-5H-4λ$^4$,5λ$^4$-dipyrrolo[1,2-c:2',1'-f][1,3,2]diazaborinine (BODIPY derivative) (280 mg, 0.864 mmol), 3,4-Dihydroxy benzaldehyde (119.3 mg, 0.864 mmol), Glacial acetic acid (0.53 ml) and Piperidine (0.65 ml) were refluxed in 10 ml toluene in a dean-stark apparatus for 3 h. Crude compound was then evaporated under vacuum and then it was purified by silica gel column chromatography using 5% Ethylacetate in Dichloromethane to get pink colour SF-1 (yield=18%). 1H NMR (400 MHz, CD$_3$OD, δ ppm, J in Hz): 7.50 (3H, m, Ar—H), 7.46 (1H, J=15.89 Hz (CH═C)), 7.27-7.25 (2H, m), 7.23 (1H, d, J=16.38 Hz (CH═CH)), 7.14 (1H, d, J=1.96 Hz), 6.94 (1H, dd, J=1.96 Hz, J=8.07 Hz), 6.80 (1H, d, J=8.07 Hz), 6.65 (2H, s), 6.02 (1H, s), 2.52 (3H, s), 1.39 (3H, s), 1.37 (3H, s). $^{13}$C NMR (400 MHz CD$_3$OD): 14.56, 14.65, 14.89, 114.24, 116.61, 117.02, 118.81, 121.91, 122.23, 129.55, 130.15, 130.29, 130.32, 132.03, 134.03, 136.41, 138.56, 141.36, 143.13, 144.36, 146.5, 148.52, 155.00, 155.39, (MALDI MS (M/Z)=444.7).

Example 2: General Experimental Procedure for Photo-Physical Experiments

Stock solution of probe SF-1 (1×10$^{-4}$ M) was prepared in HPLC grade Acetonitrile and the same solution was used for all the studies after appropriate dilution to 5 ml of PBS (pH 7.2) to make the effective ligand concentration of 10 µM. Unless and otherwise mentioned, 10 mM and pH 7.2 solution of aq. PBS buffer was used for all spectroscopic studies. All reactive Oxygen species and nitrogen species solutions of 1×10-2 M were prepared in PBS having pH 7.2 and used with appropriate dilution. All luminescence measurements were done using $\lambda_{Ex}$=550 nm with an emission slit width of 2/2 nm. For all biological studies, 0.6% DMSO in DMEM media was used.

Example 3: Calculation of Detection Limit

The detection limit was calculated based on the fluorescence titration. To determine the S/N ratio, the emission intensity of only SF-1 probe without addition of HOCl was measured 8 times and the standard deviation of blank measurements was determined. The detection limit (DL) of SF-1 for HOCl was determined from the following equation:

$$DL=K*Sb1/S$$

here K=2 or 3 (3 were taken in this case); Sb1 is the standard deviation of the blank solution; and S is the slope of the calibration curve.

From the graph there was a slope=2.50×109, and Sb1 value is 3.59. Thus using the formula, the Detection Limit=4.3×10$^{-9}$ M was obtained.

The in vitro cytotoxicity of SF-1 on RAW 264.7 cells were determined by conventional MTT (3-(4, 5-Dimethylthiazol-2-yl)-2, 5-diphenyltetrazolium bromide) assay. RAW 264.7 cells (5×103) were seeded in each well of a 96 well plate and cultured in a 37° C. incubator supplied with 5% $CO_2$. Cells were maintained in DMEM medium, supplemented with 10% Foetal Bovine Serum and 100 Units of Penicillin Streptomycin antibiotics. After 24 hours the cells were treated with different concentrations of the SF-1 in triplicates for 24 hours. After the treatment, cells were added with 0.5 µg/ml of MTT reagent. The plate was then incubated for 4 hours at 37° C. 100 µL of Isopropyl Alcohol was added to each well. Optical density was measured at 570 nm using Multiskan Go (Thermo Scientific) to find the concentration of the cell inhibition. IC50 value has been calculated to be >150 µM.

The formula used for the calculation of the MTT assay for evaluation of the cell viability was as follows:

Cell viability (%)=(Means of absorbance value of treated group/Means of absorbance value of untreated control)×100.

Using the same protocol an MTT assay for evaluation of the cell viability was also done for SF-2 and its IC50 value was calculated to be 110 µM.

Advantages of the Disclosure

1. Probe SF-1 specifically detects HOCl at neutral pH and at physiological condition.

2. Response of Probe SF-1 towards HOCl is very fast.

3. Owing to high fluorescence quantum yield and photo stability, it could be a candidate for high resolution microscopic imaging application to map exact localization of endogenous HOCl generation.

4. The Probe SF-1 can detect HOCL present in the Golgi bodies of the living cells.

5. The Probe SF-1 can be used under super-resolution imaging conditions, whereas commercially available Golgi tracker fails to do so.

6. The Probe SF-1 can monitor endogenous HOCl generation in living cells.

We claim:
1. A compound of formula SF1

2. The compound of claim 1, wherein a detection limit for HOCl is in the range of 4 to 5 nM in aq. PBS buffer-acetonitrile.

3. A kit for detection of HOCl comprising the compound of formula SF-1 of claim 1.

4. A process for preparation of a compound of formula SF-1 having the following structure:

SF-1 the process comprising:
i. refluxing a BODIPY derivative, 3,4-Dihydroxy benzaldehyde, glacial acetic acid and piperidine in a solvent at a temperature ranging from 110° C. to 120° C. for a period ranging from 3 to 4 hours to afford the compound of formula SF-1.

5. The process of claim 4, wherein refluxing a BODIPY derivative comprises refluxing 5,5-difluoro-1,3,7,9-tetramethyl-10-phenyl-5H-4$\lambda^4$,5$\lambda^4$-dipyrrolo[1,2-c:2',1'-f][1,3,2]diazaborinine.

6. The process of claim 4, further comprising selecting the solvent to comprise toluene.

7. A method of detecting hypochlorous acid, the method comprising:
selectively detecting hypochlorous acid (HOCl) using the following compound:

SF-1

8. The method of claim 7, wherein selectively detecting hypochlorous acid comprises selectively detecting hypochlorous acid over other reactive oxygen species (ROS) under physiological condition.

9. The method of claim 7, wherein selectively detecting hypochlorous acid comprises selectively detecting hypochlorous acid in live RAW 264.7 macrophages.

10. The method of claim 7, wherein selectively detecting hypochlorous acid (HOCl) comprises selectively detecting hypochlorous acid (HOCl) in biological systems.

* * * * *

UNITED STATES PATENT AND TRADEMARK OFFICE
CERTIFICATE OF CORRECTION

PATENT NO. : 11,319,331 B2
APPLICATION NO. : 16/609423
DATED : May 3, 2022
INVENTOR(S) : Firoj Ali et al.

It is certified that error appears in the above-identified patent and that said Letters Patent is hereby corrected as shown below:

On the Title Page
In ITEM (54),   Line 1,          change "PROBE FOR" to --A PROBE FOR--

In the Specification
Column 1,      Line 1,           change "PROBE FOR" to --A PROBE FOR--
Column 2,      Line 17,          change "Ht116 cells" to --Hct116 cells--

Signed and Sealed this
Twenty-eighth Day of February, 2023

Katherine Kelly Vidal
*Director of the United States Patent and Trademark Office*